United States Patent [19]

Rao

[11] 4,102,938
[45] Jul. 25, 1978

[54] PRODUCTION OF HYDROCARBONS BY THERMOLYSIS OF VEGETABLE OILS

[76] Inventor: Kalur Vijaya Chandra Rao, Head, PSC Division, CMG, VSSC, Trivandrum-695022, India

[21] Appl. No.: 773,544

[22] Filed: Mar. 2, 1977

[51] Int. Cl.² .............................................. C07C 1/20
[52] U.S. Cl. ................................. 260/676 R; 260/682
[58] Field of Search ............................ 260/676 R, 682

[56] References Cited

U.S. PATENT DOCUMENTS

| 2,047,945 | 7/1936 | Arnold et al. ...................... 260/682 |
| 2,093,159 | 9/1937 | Schmidt ........................... 260/676 R |
| 2,437,438 | 3/1948 | Petroff et al. .................... 260/666 R |

*Primary Examiner*—C. Davis
*Attorney, Agent, or Firm*—Haseltine, Lake & Waters

[57] ABSTRACT

Vegetable oils are thermolyzed in the presence of a silica-alumina catalyst impregnated with any one of the oxides of the transition metals of groups IIB, IIIB, IVB, VB, VIB, VIIB and VIII of the Periodic Table at temperatures ranging between 300° C and 700° C under atmospheric pressure in a fluidized bed, moving bed or fixed bed continuous tubular reactor, separating and purifying the resulting hydrocarbons.

15 Claims, 1 Drawing Figure

U.S. Patent
July 25, 1978
4,102,938
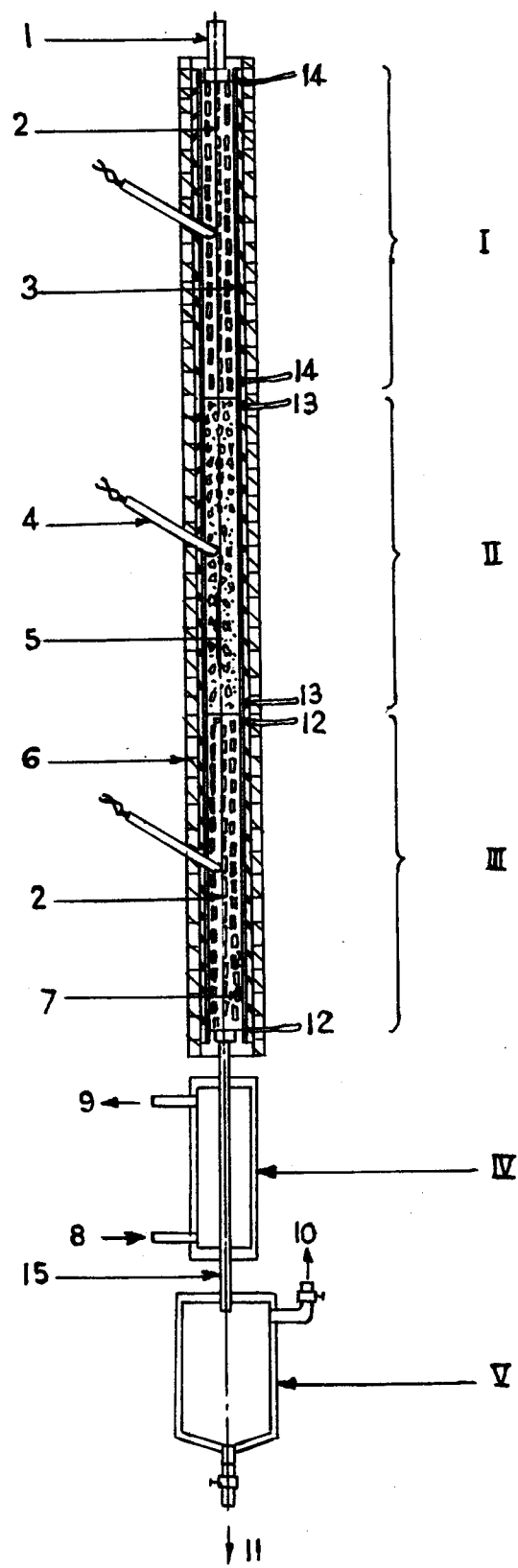

PRODUCTION OF HYDROCARBONS BY THERMOLYSIS OF VEGETABLE OILS

The present invention is concerned with a process for producing hydrocarbons from vegetable oils and the hydrocarbons so produced.

Production of hydrocarbons starting from vegetable oils had been attempted earlier and the work carried out in this line can be classified into four categories, viz (a) conversion of vegetable oils to soaps by hydrolysis, followed by distillation of the soap, resulting in the formation of hydrocarbons, (b) hydrolysis of oils to get fatty acids and decarboxylation of the fatty acids in the presence of catalysts to get hydrocarbons, (c) direct decarboxylation of oils in the presence of catalysts to get hydrocarbons and (d) cracking of oils under pressure. The present invention falls in the category of (c); and the earlier work belonging to this category is described in the following paragraph.

A. Mailhe (Compt. rend. 173, 358–9, 1921; Amn. Chim. 17, 304–32, 1922; J. Usines Gaz. 47, 65–8, 1923, Comp. rend 177, 202–4, 1923; J. Usines Gaz. 46, 289–92, 1922; Chaleur et. Industries, 5, 3–5, 1924; J. Usines Gaz. 47, 321–4, 1923; Compt. rend. 177, 329–31, 1924) converted vegetable oils into hydrocarbons using metallic salts such as $MgCl_2$, $ZnCl_2$, Copper turnings and MgO at temperatures ranging from 300° to 700° C. In all the cases, in addition to hydrocarbons, he observed the presence of oxygenated compounds (as free acids) in the product. A Japanese Pat. No. 40,623; claims the conversion of vegetable oils to a greenish fluorescent liquid along with some free fatty acids, in the presence of Japanese clay catalyst at 900° C. G. Obarhausen, Fr. No. 682, 852 and Brit. No. 340, 107, converted the vegetable oils like soyabean, peanut into hydrocarbons in the presence of Fe, Zn or Cu and used them as motor fuel. However, some oxygenated compounds have been reported in the products. K. Ping and other Chinese workers, (J.Chinese Chem. Soc. 3, 281–7, 1935; Chinese industry 1, 2021–39, 1935; J.Chem. Eng. China 3, 201–10, 1936; J.Chem. Eng. China 3, 231–9, 1936; J. Chinese Chem. Soc. 8, 100–7, 1941; J.Chinese Chem. Soc. 18, 95–102, 1951) have reported conversion of vegetable oils into petroleum type of hydrocarbons using $AlCl_3$, CaO, NaOH, $ZnCl_2$, $CaCl_2$, Fe, $Fe_2O_3$ and $Ca(OH)_2$ as catalysts at temperatures between 250° and 1000° C. The products obtained are reported to be gasoline (which was inferior in knock-rating), kerosene, high boiling fractions and unreacted fats. M. Friedwalk, (Rev. Petrolifeze No. 734, 597–9, 1937) subjected oil seeds to temperature of the order of 500° to 550° C and distilled the resulting oil in the presence of a catalyst and obtained a product containing 50% crude oil, 15 to 20% coke, the rest unreacted fats. Edovard G M Lese Brit. Pat. No. 485, 123 described the production of blackish greeen fluorescent oil, smelling like petroleum, when fats, vegetable oils, palm oil and fish oil were subjected to distillation at 250° to 600° C in the presence of alkali salts, weak acids, amphoteric oxides, alkali silicates, aluminates, carbonates, titanates, vanadates, uranates and plumbates. M. R. Mandalekar et. al (J.Sci.Ind.Research, India, 5B, 45–7, 1946; J.Ind. Chem. Soc. Ind. News, Ed.10, 1–16, 1947) described the conversion of peanut, castor, cotton and coconut oils by vapor cracking using fire-clay as catalyst. In the products, they obtained olefins and saturated hydrocarbons. Further references are seen in the literature regarding conversion of vegetable oils to hydrocarbon products, contaminated with oxygenated compounds, utilizing different methods like catalysis by Bentonite clay (Genoziz Nefia Gaza, Moscow, 146–51, 1967), by irradiation (Bertold Inst. Chem. tech. and Tech. Uni Muen Chen Preising Weihenstephan Ger. 2 Leibension Utans Forch. 55 (J.), 1–9, 1974), by pressure autoclaving (Ind. Eng. Chem. 24, 1429, 1932; J.Chinese Chem. Soc. 4, 157–71, 1936), by using sodium carbonate and acetate together with iron (Non Petrole roumain 39, 699–702, 1938). Dalal and Mehta (J.Indian Chem. Soc. Ind. News. Ed. 2, 213–45, 1939) have reported that by cracking of coconut oil, ground nut oil, sesame oil and mahua oil in the presence of iron at 300° to 500° C, followed by distillation in the presence of $ZnCl_2$ under pressure of 45 to 300 psi, products like liquid hydrocarbons together with solid residues are obtained. Fa Wu Cheng (Che. & Met. Eng. 52, 1, 99, 1945), Y. C. Sun (J. Chinese Chem. Soc. 8, 108–11, 1941) and Tsung, Shih Le and Liu shang Tsai (J.Chinese Chem. Soc. 6, 1–7, 1938) obtained a gasoline type product together with high boiling fractions by pressure cracking of tung oil, mustard oil, cotton seed oil, oleic acid, linoleic acid and palmitic acid.

According to this invention there is provided a process for producing hydrocarbons from vegetable oils which comprises thermolyzing the said oils in presence of silica-alumina catalyst impregnated with any one of the oxides of the transition metals of groups IIA, IIIB, IVB, VB, VIB, VIIB & VIII of the periodic table at temperatures ranging between 300° and 700° C under atmospheric pressure in a fluidized bed or fixed bed continuous tubular reactor, separating and purifying the resulting hydrocarbons.

A process for producing hydrocarbons as described above wherein the resulting product is free from oxygenated compounds other than carbon dioxide and water.

A process for producing hydrocarbons as described above wherein the resulting product is condensed to separate the gaseous hydrocarbons from the liquid hydrocarbons.

A process for producing hydrocarbons as described above wherein 95% of the liquid hydrocarbons so obtained boil below 400° C.

A process for producing hydrocarbons as described above wherein the said vegetable oils include both edible and nonedible oils having the general formulae.

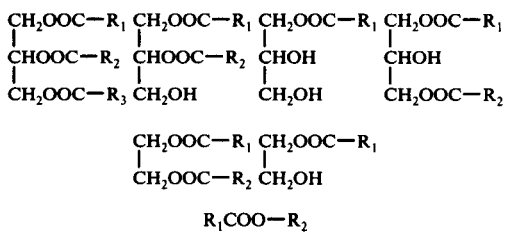

where $R_1$, $R_2$ and $R_3$ stand for hydrocarbon radicals, either saturated, unsaturated, branched chain, straight chain or cyclic hydrocarbon radicals having 6 to 24 carbon atoms.

A process as described above wherein the ratio of liquid hydrocarbons to gaseous hydrocarbons per given quantity of vegetable oil can be controlled by adjusting the liquid hourly space velocity (LHSV) of the vegetable oils at a given temperature, increase of LHSV increasing the liquid hydrocarbon content.

A process as described above wherein the ratio of liquid to gaseous hydrocarbons per given quantity of vegetable oil can be controlled by adjusting the reaction temperature at a given LHSV, increase of temperature decreasing the liquid hydrocarbon content.

A process as described above wherein a silica-alumina catalyst impregnated with oxides of molybdenum, Zirconium and Titanium is used.

A process as described above wherein silica-alumina catalysts impregnated with oxides of platinum, chromium, nickel, magnesium, vanadium and cerium are used.

A process as described above wherein the gaseous hydrocarbons contain $C_3$ and $C_4$ olefins which constitute 50 to 70% by volume of the gaseous hydrocarbons.

A process as described above wherein the catalyst is regenerated by passing air at temperatures 400° to 600° C to regain the catalytic activity.

When vegetable oils are made to come into contact with catalysts (described later) at reaction temperatures of 300° to 700° C preferably 400° to 500° C under atmospheric pressure, they give rise to gaseous and liquid hydrocarbons. On increasing the reaction temperature from 300° to 700° C, the yield of liquid hydrocarbons decreases and that of gaseous hydrocarbons increases. When operated within the stipulated conditions, no oxygen containing compounds, other than $H_2O$ and $CO_2$, are formed. The liquid product is practically free from oxygenated compounds. $C_3$ and $C_4$ olefins constitute 50 to 70% by volume of the gaseous hydrocarbons, the rest being saturates. Traces of $C_5$ hydrocarbons can be detected in the gaseous stream. The percentage yield of liquid hydrocarbons increases and that of gaseous hydrocarbons decreases when the liquid hourly space velocity (LHSV) of the vegetable oil fed to the continuously operating reactor is increased, keeping the other experimental parameters like temperature and pressure constant. The liquid hydrocarbons, when subjected to distillation, yield four different cuts; from initial boiling point (IBP) to 200° C (15 to 60% by volume), 200° to 250° C (10 to 30% by volume), up to 250° C under vacuum (10 to 30% by volume) and higher boiling liquids (10 to 30% by volume). In all the cases, the liquid hydrocarbons, when subjected to IBP distillation according to ASTM D1078, Part 20 (1970) give 95% products distilling below 380° C. Thus, the present invention describes a process to get light petroleum like hydrocarbons irrespective of the vegetable oil used.

The catalyst used in these reactions can be prepared as follows:

Aqueous sodium silicate solution (10 to 70% by weight in water) is heated to 40° to 100° C and boiling mineral acid, like $HNO_3$ or $H_2SO_4$ (40 to 80% concentration), is added till the pH of the solution is between 4 and 1 when hydrated silica is precipitated. Aluminum salt solution, either as sulfate nitrate, or an aluminate is added in hot condition to the precipitated hydrated silica solution. Impregnating transition metal salt solution is added to the above, under agitation. The solution is allowed to stand for 10 to 15 hrs. Then the pH of the solution is increased to 6 to 7 by adding an alkali solution, such as NaOH, $NH_4OH$. In the presence of already precipitated hydrated silica, the aluminum and the impregnating transition metal get precipitated as hydroxides under these conditions. The solution is allowed to stand for a period of 24 to 96 hrs. The precipitate from this solution is recovered by centrifuging and is then washed with distilled water till it is free from sulfate ions. The filtered precipitate (gel) containing 40 to 90% moisture is extruded into strands and the gel strands are dried at 100° to 120° C for 24 hrs. The gel strands shrink after drying and are cut into 5 to 10 mm long pieces and sintered at 500° to 600° C for 4 to 8 hrs. The catalyst, after sintering, is allowed to cool and is stored.

A typical reactor arrangement is shown in the accompanying drawing and the process procedure is as follows:

The reactor used for the conversion of vegetable oils into hydrocarbons, is of the fixed bed type but the method is equally applicable to moving and fluidized bed type reactors. The reactor shown in the accompanying drawing is 1¼ inch stainless steel tube 7. It consists of three zones namely preheating zone I, reaction zone II and post reaction zone III. The preheating and post reaction zones contain stainless steel beads 2. The reaction zone is filled with catalyst 5. The three zones are heated independently by heating coils 3; the preheating zone by coil numbered 14, reaction zone by coil numbered 13 and the post reaction zone by coil numbered 12. The temperature of each zone is measured by independent thermocouples 4. When these zones attain the preset temperatures, the vegetable oil is fed into the reactor through the inlet 1. The oil feed rate is controlled by means of a feed valve (not in the figure). The temperatures in the three zones are maintained at the required levels. To prevent heat loss, the reactor system is insulated 6.

The catalyst can convert vegetable oils roughly up to 15 times of its volume before regeneration of the catalyst. The liquid products are tested spectroscopically, say, every fifteen minutes for the presence of oxygenated compounds. The oil feed is stopped on the oxygenated compound being detected and the catalyst is regenerated by passing air through the catalyst bed by keeping the temperature always below 600° C either by controlling the flow rate of air let in or by cooling the catalyst bed externally. The completion of the catalyst regeneration reaction is indicated by the decrease in temperature of the catalyst bed. On completion of regeneration, the passage of air into reactor is discontinued and vegetable oil feed for conversion is started.

The products from the reactor pass through a condenser IV through a stainless tube 15. The condenser is cooled by means of water entering through the inlet 8 and leaving through the outlet 9. The cooled, condensed products from the condenser pass through a separator V. Here the uncondensed gases are drawn out through the gas outlet 10 and the liquids are drawn out through a bottom outlet 11. The condensed liquid products contain hydrocarbons similar to those present in petroleum crude. The gaseous products are passed through alkali solution (KOH solution) to remove $CO_2$ and then through dried silica gel to remove moisture to obtain pure dry gaseous hydrocarbons.

The following examples illustrate the typical methods of preparation of the catalyst and converting different types of oils into hydrocarbons:

EXAMPLE 1

Catalyst (TISIAL-1) Preparation 2.8 kg of sodium silicate (containing 34% silica by weight) is diluted with 14 liters of distilled water and heated to 90° C. Nitric acid (69%), diluted with an equal volume of distilled water, is heated to boiling and added to the hot sodium silicate solution under agitation till

TABLE 5

| Feed | : Rubber seed oil | | | | |
|---|---|---|---|---|---|
| Temperature | : 480° C | | | | |
| LHSV | : 0.205 | | | | |
| | Fresh catalyst | 1st regeneration | 2nd regeneration | 3rd regeneration | 4th regeneration |
| kg of oil cracked/kg of catalyst | 10.6 | 10.6 | 10.4 | 10.4 | 10.3 |
| liquid hydrocarbons (% vol of the feed) | 59.5 | 54.5 | 56.5 | 60.0 | 57.2 |
| Gaseous products lit (at NTP)/ lit of feed | 204.0 | 189.0 | 190.0 | 193.0 | 218.0 |
| IBP of liquid hydrocarbons (° C) | 38.0 | 38.0 | 40.0 | 40.0 | 38.0 |
| Vol % of fractions of total liquid products: | | | | | |
| IBP to 200° C | 58.0 | 54.0 | 57.0 | 56.0 | 58.0 |
| 200° to 250° C | 20.0 | 21.0 | 20.5 | 21.5 | 21.0 |
| Under vacuum up to 250° C | 10.0 | 11.0 | 12.0 | 11.5 | 10.5 |

We claim:

1. A process for producing hydrocarbons from vegetable oils which comprises thermolyzing the said oils in the presence of a silica-alumina catalyst impregnated with any one of the oxides of the transition metals of groups IIA, IIIB, IVB, VB, VIB, VIIB and VIII of the Periodic Table at temperatures ranging between 300° and 700° C under atmospheric pressure in a fluidized bed, moving bed or fixed bed continuous tubular reactor, separating and purifying the resulting hydrocarbons.

2. A process for producing hydrocarbons as claimed in claim 1 wherein the resulting product is free from oxygenated compounds other than carbon dioxide and water.

3. A process for producing hydrocarbons as claimed in claim 2 wherein the resulting product is condensed to separate the gaseous hydrocarbons from the liquid hydrocarbons.

4. A process for producing hydrocarbons as claimed in claim 1 wherein 95% of the liquid hydrocarbons so obtained boil below 400° C.

5. A process for producing hydrocarbons as claimed in claim 1 wherein the said vegetable oils comprise both edible and nonedible oils having the general formulae

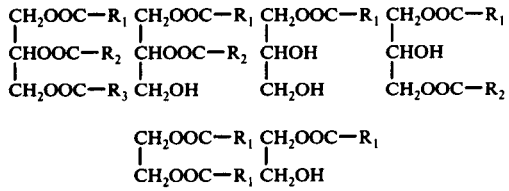

$R_1COO-R_2$ where $R_1$, $R_2$ and $R_3$ stand for hydrocarbon radicals either saturated, unsaturated, branched chain, straight chain or cyclic hydrocarbon radicals having 6 to 24 carbon atoms.

6. A process as claimed in claim 3 wherein the ratio of liquid hydrocarbons to gaseous hydrocarbons per given quantity of vegetable oil is controlled by adjusting the liquid hourly space velocity (LHSV) of the oil feed at a given temperature, increase of LHSV increasing the liquid hydrocarbon content.

7. A process as claimed in claim 3 wherein the ratio of liquid to gaseous hydrocarbons per given quantity of vegetable oil is controlled by adjusting the reaction temperature at a given LHSV of the oil feed, increase of temperature decreasing the liquid hydrocarbon content.

8. A process as claimed in claim 1 wherein a silica-alumina catalyst impregnated with any one of the oxides of molybdenum, zirconium or titanium is used.

9. A process as claimed in claim 1 wherein a silica-alumina catalyst impregnated with any one of the oxides of platinum, chromium, nickel, magnesium, vanadium and cerium is used.

10. A process as claimed in claim 1 wherein olefins having $C_3$ to $C_4$ carbon atoms constitute 50 to 70% by volume of the gaseous hydrocarbons produced.

11. A process as claimed in claim 1 wherein the catalyst is regenerated by passing air at a temperature of 400° to 600° C till the deposited carbon is completely oxidized.

12. A process as claimed in claim 1 wherein the oil is selected from the group consisting of rubber seed oil, mahua oil, karanja oil, sal oil, punna oil, ground nut oil, sesame oil and castor oil.

13. A process as claimed in claim 12 wherein the temperature is 480° C.

14. A process as claimed in claim 13 wherein the transition metal oxide in the catalyst is titanium oxide.

15. A process as claimed in claim 1 wherein the oil is rubber seed oil, the transition metal oxide in the catalyst is molybdenum oxide or titanium oxide and the temperature is 420° - 480° C.

* * * * *

UNITED STATES PATENT AND TRADEMARK OFFICE
CERTIFICATE OF CORRECTION

PATENT NO. : 4,102,938                                    Page 1 of 2

DATED : July 25, 1978

INVENTOR(S) : Kalur Vijaya Chandra Rao

It is certified that error appears in the above-identified patent and that said Letters Patent are hereby corrected as shown below:

The attached Columns 5 thru 8 should be inserted before Columns 9 and 10.

This certificate applys to the GRANT, exclusively.

Signed and Sealed this

Tenth Day of July 1979

[SEAL]

Attest:

Attesting Officer

LUTRELLE F. PARKER
Acting Commissioner of Patents and Trademarks the pH comes down to around 1 (about 1.8 liters of dilute boiling nitric acid is required) when hydrated silica is precipitated. 1.050 kg of aluminum sulfate (Al$_2$(SO$_4$)$_3$.16H$_2$O) dissolved in 3.5 liters of distilled water is added to the precipitated hydrated silica solution followed by 82.5 ml of titanyl sulfate solution (concentration 8.6 g of TiO$_2$ per liter of solution) with agitation. The agitation is continued for 30 to 35 minutes. The solution is allowed to stand for 15 hrs. NH$_4$OH (12.5% concentration) is added to the above solution while stirring until the pH increases to 6 to 6.5 (around 2.4 liters of ammonia solution is required). In the presence of already precipitated hydrated silica, the aluminum hydroxide together with titanium hydroxide is precipitated under these conditions. The precipitates in suspension are thoroughly agitated for half an hour and allowed to stand for 96 hrs. The precipitate is filtered and washed with acidified distilled water (acidified with HNO$_3$ to a pH of 4 to 5) till the washings indicate the absence of SO$_4$ ion as tested by BaCl$_2$ solution. (Approximately 50 liters of distilled water is required). The precipitate (gel) containing 80 to 85% moisture is extruded through a 6 mm diameter die. The gel strands are dried for 24 hours at 110° C. The strands shrink to around 4 to 5 mm diameter after drying. The dried strands are cut into around 8 to 10 mm pieces and sintered at 600° C for 6 hrs. The heating to 600° C and cooling are carried out gradually. When the catalyst strands are cooled down to room temperature, they exhibit sufficient mechanical properties to withstand the reaction conditions. The catalyst thus obtained will weigh around 1 kg.

The catalyst made as described above was used as described under the typical reactor arrangement and process procedure, described earlier, for the conversion of vegetable oils into hydrocarbons. The results are given under Example-5, Table-1.

EXAMPLE 2

Catalyst (TISIAL-2) Preparation

The precipitation of hydrated silica is carried out in the same manner as explained in Example 1. The pH of this solution is kept at around 1. 435 g of sodium aluminate dissolved in 3.5 liters of distilled water is added to the precipitated hydrated silica solution under agitation. The pH of the solution is raised to around 10. The pH is brought down to around 1 by adding boiling dilute nitric acid (69% acid diluted with an equal volume of distilled water). 82.5 ml of titanyl sulfate solution (concentration 8.6 g of TiO$_2$ per liter of solution) is added to this under agitation. The solution is stirred thoroughly for about 30 minutes and allowed to stand for 15 hrs. 12.5% ammonia solution is slowly added to this solution till the pH comes to 6 to 6.5 (about 2.1 liters of ammonia is required). The aluminum and titanium hydroxides are precipitated under these conditions. The precipitated solution is stirred thoroughly for about 30 minutes and allowed to stand for 90 hrs.

The further processing of the precipitated gel is the same as given in Example 1.

The catalyst made as described above was used as described under the typical reactor arrangement and process procedure, described earlier, for the conversion of vegetable oils into hydrocarbons. The results are given under Example 5, Table 1.

EXAMPLE 3

Catalyst (ZIRSIAL) Preparation

The procedure for the preparation of this catalyst is the same as explained in Example 1 except that in the place of titanyl sulfate, zirconium nitrate solution prepared in the following manner is added.

7 g of zirconium metal is dissolved in concentrated nitric acid (by HF treatment). Ammonia solution is added to this to precipitate zirconium as its hydroxide. The precipitate is washed with distilled water till it is free from fluoride ions and then dissolved in dilute nitric acid (1 volume of 69% acid mixed with 3 volumes of distilled water) to obtain zirconium nitrate solution.

The catalyst made as described above was used as described under the typical reactor arrangement and process procedure, described earlier, for the conversion of vegetable oils into hydrocarbons. The results are given under Example 5, Table 1.

EXAMPLE 4

Catalyst (MOSIAL) Preparation 300 g of sodium silicate (containing 34% silica by weight) is dissolved in 2 liters of distilled water and heated. 7 g of ammonium molybdate is dissolved in 500 ml of distilled water and this solution is added to the hot sodium silicate solution. This mixed solution is heated to 90° C and boiling nitric acid solution (69% acid diluted with an equal volume of distilled water) is slowly added to this with agitation till the pH is brought down to around 1. Hydrated silica is precipitated at this pH. 150 g of aluminum sulfate (Al$_2$(SO$_4$)$_3$. 16H$_2$O) is dissolved in 500 ml of distilled water and added to the solution at pH 1 and stirred thoroughly for about 20 minutes. The solution is allowed to stand for 15 hrs. 12.5% ammonia solution is added to the solution while stirring until the pH increases to 5 to 6 (about 15 ml of ammonia solution is required) when the hydroxides of aluminum and molybdenum are precipitated. The precipitate (gel) is allowed to stand for 15 hrs. The gel is washed with 6 liters of acidified distilled water (acidified with HNO$_3$ to a pH of 4 to 5). The gel containing 80 to 85% water is extruded and dried in the oven for 24 hrs at 110° C. The further processing of the catalyst is the same as given in the Example 1.

The catalyst made as described above was used as described under the typical reactor arrangement and process procedure, described earlier, for the conversion of vegetable oils into hydrocarbons. The results are given under Example 5, Table 1.

By adopting similar procedures catalysts containing the following impregnation metals in place of titanium zirconium, etc., have been prepared and the resultant catalysts have been named as given in parenthesis below:

(a) Platinum as oxide   (PLATSIAL)
(b) Chromium as oxide   (CHROSIAL)
(c) Nickel as oxide   (NISIAL)
(d) Magnesium as oxide   (MAGSIAL)
(e) Vanadium as oxide   (VASIAL)
(f) Cerium as oxide   (CESIAL)

The catalysts made as described above were used as described under the typical reactor arrangement and process procedure, described earlier, for the conversion of vegetable oils into hydrocarbons. The results are given under Example 5, Table 1.

EXAMPLE 5

Conversion of Rubber Seed Oil Into Hydrocarbons

Experiments were conducted with rubber seed oil as feed, at liquid hourly space velocity of 0.3 lit/lit/hr, at 480° C using the different catalysts mentioned earlier in the manner described under the typical reactor arrangement and process procedure. The results are given in Table 1.

TABLE - 1

| Sl No | Catalyst used | LHSV lit/lit/hr. | % of liquid hydrocarbons (vol % of feed) | Water (vol % of feed) | Gaseous products in lit (at NTP)/lit of feed |
|---|---|---|---|---|---|
| 1 | TISIAL-1 | .35 | 55.6 | 2.73 | 188 |
| 2 | TISIAL-2 | .29 | 50.0 | 3.00 | 208 |
| 3 | ZIRSIAL | .23 | 51.8 | 2.10 | 181 |
| 4 | MOSIAL | .28 | 53.2 | 2.00 | 231 |
| 5 | PLATSIAL | .24 | 46.8 | 2.10 | 156 |
| 6 | CHROSIAL | .23 | 20.6 | 2.00 | 403 |
| 7 | NISIAL | .24 | 52.0 | 2.00 | 217 |
| 8 | MAGSIAL | .26 | 64.5 | 2.10 | 121 |
| 9 | VASIAL | .28 | 51.3 | 2.15 | 166 |
| 10 | CESIAL | .28 | 55.0 | 2.08 | 208 |

The organic liquid products obtained are found to be free from oxygenated compounds as per the spectroscopic analysis. The gaseous products are found to contain $CO_2$ around 30% by weight.

EXAMPLE 6

Effect of Temperature on Product Pattern

The organic liquid products obtained are found to contain no oxygenated compounds when analyzed spectroscopically. The gaseous products are found to contain $CO_2$ around 30% by weight.

EXAMPLE 7

Effect of Liquid Hourly Space Velocity on Product Pattern

Experiments conducted at different liquid hourly space velocities using rubber seed oil as feed at 420° C are given in Table 3.

TABLE - 3

| Feed | : | Rubber seed oil |
| Reaction temperature | : | 420° C |

| Catalyst | LHSV | Liquid hydrocarbons (vol % of feed) | Gaseous products in lit(at NTP)/ lit of feed | Water (vol % of feed) |
|---|---|---|---|---|
| MOSIAL | .283 | 66.0 | 141 | 2.1 |
|  | .400 | 71.8 | 96 | 2.0 |

The organic liquid products are found to be free from oxygenated compounds when analyzed spectroscopically. The gaseous products are found to contain $CO_2$ around 30% by weight.

EXAMPLE 8

Conversion of Different Oils Into Hydrocarbons

Experiments conducted with different oils and oil mixtures using TISIAL-1 Catalyst at 480° C are summarized in Table 4.

TABLE - 4

| Catalyst | : | TISIAL-1 |
| Reaction temperature | : | 480° C |

| | | Liquid hydrocarbons | | | | Gaseous products | |
|---|---|---|---|---|---|---|---|
| Sl No | Feed | Total (vol % of feed) | IBP (° C) | IBP to 200° C | 200 to 250° C | Up to 250° C under vacuum | in it (at NTP) /lit of feed | Water (% vol of feed) |

| Sl No | Feed | Total (vol % of feed) | IBP (° C) | IBP to 200° C | 200 to 250° C | Up to 250° C under vacuum | in it (at NTP) /lit of feed | Water (% vol of feed) |
|---|---|---|---|---|---|---|---|---|
| | | | | (% of total liquid hydrocarbons) | | | | |
| 1 | Rubber seed oil | 47.4 | 38.0 | 55.0 | 24.0 | 18.0 | 237 | 2.2 |
| 2 | Mahua oil | 55.5 | 40.0 | 52.0 | 18.0 | 17.0 | 188 | 2.0 |
| 3 | Karanja oil | 56.8 | 40.0 | 53.0 | 20.0 | 17.5 | 200 | |
| 4 | Sal oil | 49.7 | 37.0 | 51.0 | 16.0 | 24.0 | 142 | 1.8 |
| 5 | Rubber seed + Karanja + Punna oils (1:1:1) | 46.4 | 41.0 | 55.0 | 18.0 | 18.0 | 188 | 1.5 |
| 6 | Punna oil | 50.0 | 40.0 | 50.0 | 17.0 | 20.0 | 222 | 0.6 |
| 7 | Ground nut oil | 50.6 | 40.0 | 57.0 | 17.0 | 12.0 | 188 | 0.5 |
| 8 | Sesame oil | 55.0 | 40.0 | 50.0 | 16.0 | 14.0 | 176 | 1.0 |
| 9 | Castor oil | 58.0 | 42.0 | 53.5 | 14.6 | 14.0 | 181 | 3.4 |

Experiments conducted at different reaction temperatures using rubber seed oil, as feed, are summarized in Table 2.

TABLE - 2

| Feed | : | Rubber seed oil | | |

| Catalyst | LHSV lit/lit hr | Reaction Temperature | % of liquid hydrocarbons (% vol of feed) | Gaseous products in lit (at NTP)/ lit of feed | Water (vol % of feed) |
|---|---|---|---|---|---|
| TISIAL-1 | .35 | 480° C | 55.6 | 188 | 3.73 |
|  | .35 | 420° C | 65.0 | 128 | 3.00 |
| MOSIAL | .283 | 480° C | 53.2 | 231 | 2.00 |
|  | .283 | 420° C | 66.0 | 141 | 2.10 |

EXAMPLE 9

Catalyst Regeneration

Table 5 gives the conditions of regeneration and details of a number of regenerations carried out and the total quantity of oil converted in a straight run by 1 kg of catalyst.